US007825160B2

(12) United States Patent
Wilson et al.

(10) Patent No.: US 7,825,160 B2
(45) Date of Patent: Nov. 2, 2010

(54) (BIPHENYL) CARBOXYLIC ACIDS AND DERIVATIVES THEREOF

(75) Inventors: Francis Wilson, Welwyn Garden City (GB); Alison Reid, Cottenham (GB); Valerie Reader, Linton (GB); Richard John Harrison, Cambridge (GB); Mihiro Sunose, Papisford (GB); Remedios Hernandez-Perni, Stalybridge (GB); Jeremy Major, Cambridge (GB); Cyrille Boussard, Saffron Walden (GB); Kathryn Smelt, London (GB); Jess Taylor, Hertfordshire (GB); Adeline Leformal, Saffron Walden (GB); Andrew Cansfield, Harston (GB); Svenja Burckhardt, Boxworth (GB)

(73) Assignee: Cellzome Limited (GB)

(*) Notice: Subject to any disclaimer, the term of this patent is extended or adjusted under 35 U.S.C. 154(b) by 408 days.

(21) Appl. No.: 11/665,760

(22) PCT Filed: Oct. 21, 2005

(86) PCT No.: PCT/EP2005/011349

§ 371 (c)(1),
(2), (4) Date: Nov. 8, 2007

(87) PCT Pub. No.: WO2006/045554

PCT Pub. Date: May 4, 2006

(65) Prior Publication Data

US 2009/0118289 A1    May 7, 2009

Related U.S. Application Data

(60) Provisional application No. 60/642,100, filed on Jan. 10, 2005.

(30) Foreign Application Priority Data

Oct. 21, 2004   (EP) ................................. 04025003
Nov. 4, 2004    (EP) ................................. 04026125

(51) Int. Cl.
*A01N 37/10*   (2006.01)
*A61K 31/19*   (2006.01)
*A01N 37/08*   (2006.01)
*A01N 53/00*   (2006.01)
*A61K 31/557*  (2006.01)
*C07C 63/00*   (2006.01)
*C07C 65/00*   (2006.01)
*C07C 63/33*   (2006.01)
*C07C 63/333*  (2006.01)
*C07C 61/04*   (2006.01)
*C07C 61/16*   (2006.01)
*C07C 62/00*   (2006.01)

(52) U.S. Cl. ...................... 514/570; 514/572; 514/573; 562/405; 562/492; 562/503; 562/505; 562/508

(58) Field of Classification Search ................. 514/188, 514/210.01, 211.01, 212.01, 218, 222.2, 514/228.8, 241, 247, 277, 359, 570, 572, 514/573; 562/405, 466, 465, 469, 492, 503, 562/505, 506, 508
See application file for complete search history.

(56) References Cited

U.S. PATENT DOCUMENTS 6,869,975 B2 * 3/2005 Abe et al. ..................... 514/568

FOREIGN PATENT DOCUMENTS

WO     2004/073705 A1    9/2004

OTHER PUBLICATIONS

De Felice et. al., Cellular and Molecular Neurobiology, 2002, Plenum Publishing Corp., vol. 22, pp. 545-563.*
Haruhiko Akiyama et al., "Inflammation and Alzheimer's Disease", Neurobiology of Aging 21 21 (2000) pp. 383-421, Open peer commentary.
Patrick L. NcGeer et al., "Arthritis and anti-inflammatory agents as possible protective factors for Alzheimer's disease: A review of 17 epidemiologic studies", Neurology 1996;47, pp. 425-432.
J. Rogers et al., "Clinical trial of indomethacin in Alzheimer's disease", Neurology Aug. 1993; 43, pp. 1609-1611.
J.C. Anthony et al., "Reduced prevalence of AD in users of NSAIDs and H2 receptor antagonists" The Cache County Study, Neurology 2000; 54 pp. 2066-2071.
Walter F. Stewart et al., "Risk of Alzheimer's disease and duration of NSAID use", Neurology 1997; 48, pp. 626-632.
T. Veld et al., "NSAIDs and Incident Alzheimer's Disease. The Rotterdam Study", Neurobiology of Aging, vol. 19, No. 6, pp. 607-611, 1998.
Sascha Weggen et al., "A subset of NSAIDs lower amyloidogeic AB42 independently of cyclooxygenase activity", Nature, vol. 414, Nov. 8, 2001, pp. 212-216.
T. Morihara et al., Rapid Communication "Selective inhibition of AB42 production of NSAID R-enantiomers", 2002 International Society for Neurochemistry, Journal of Neurochemistry, 83, pp. 1009-1012.
Jason L. Eriksen et al., "NSAIDs and enantiomers of flurbiprofen target y-secretase and lower AB42 in vivo", The Journal of Clinical Investigation, Aug. 2003, vol. 112, No. 3, pp. 440-449.
Yoshihiko Yoshimoto et al., "Nonsteroidal Antiinflammatory Agents. 1. 5-Alkoxy-3-biphenylylacetic Acids and Related Compounds as New Potential Antiinflammatory Agents", Journal of Medicinal Chemistry, 1977, vol. 20, No. 5, pp. 709-714.

* cited by examiner

*Primary Examiner*—Sreeni Padmanabhan
*Assistant Examiner*—Sarah Pihonak
(74) *Attorney, Agent, or Firm*—J.A. Lindeman & Co., PLLC

(57) ABSTRACT

The present invention relates to compounds having the general formula (I) with the definitions of A, X, $R_1$-$R_6$ given below, and/or a salt or ester thereof. Furthermore the invention relates to the use of said compounds for the treatment of Alzheimer's disease and their use for the modulation of γ-secretase activity.

10 Claims, No Drawings

(BIPHENYL) CARBOXYLIC ACIDS AND DERIVATIVES THEREOF

The present invention relates to compounds having the general formula (I) with the definitions of A, X, $R_1$-$R_6$ given below, and/or a salt or ester thereof.

Furthermore, the invention relates to the use of said compounds for the treatment of Alzieimer's disease and their use for the modulation of γ-secretase activity.

Alzheimer's disease is the most common form of age-related neurodegenerative illness.

It is primarily, but not exclusively, associated with aging and presents clinically not only by progressive loss of memory, cognition, reasoning and judgement, but also by emotional instability and gradually leads to profound mental deterioration and death.

The defining pathological hallmarks of Alzheimer's disease are the presence of neurofibrillary tangles and amyloid plaques in the brain, which are also thought to play a central role in the pathogenesis of the disease.

These plaques mainly consist of peptides formed as cleavage products of the amyloid precursor protein (APP), a 695 amino acid protein, whose function so far has only been the subject of various hypotheses.

APP is processed in two steps; a first step (catalyzed by β-secretase) gives rise to a secreted peptide and a membrane-bound C99-fragment.

C99 is a substrate for the second proteolytic activity mediated by γ-secretase resulting, inter alia, in the production of peptides in the range of 37-42 residues.

The amount of the longer isoform, Aβ42, is selectively increased in patients carrying certain mutations in a particular protein (presenilin), and these mutations have been correlated with early-onset familial Alzheimer's disease.

Therefore, Aβ42 is believed by many to be the main culprit of the pathogenesis of Alzheimer's disease.

It has now become clear that the γ-secretase activity cannot be ascribed to a single particular protein, but is in fact associated with an assembly of different proteins comprising Aph1, Nicastrin, Presenilin and Pen-2 (reviewed by De Strooper (2003) Neuron 38, 9)

Thus, although the molecular mechanism of the 2nd cleavage-step has remained elusive until present, the γ-secretase-complex has become one of the prime targets in the search for compounds for the treatment of Alzheimer's disease.

Other hints in the search for novel treatments came from epidemiological studies, an example being the finding that the uptake of certain non-steroidal anti-inflammatory drugs ("NSAIDs") seems to correlate with a reduced risk of developing Alzheimer's disease (Akiyama et al (2000) Neurobiol. Aging 21, 383; McGeer et al (1996) Neurology 47, 425; Rogers et al (1993) Neurology 43, 1609; Anthony et al (2004) Neurology 54, 2066; Stewart et al (1997) Neurology 48, 626; In't Veld et al (1999) Neurobiol. Aging 19, 607).

Indeed, this finding was recently supported by biochemical studies in which an effect of certain NSAIDs on γ-secretase was shown (Weggen et al (2001) Nature 414, 6860, 212; Morihara et al (2002) J. Neurocherm 4, 1009; Eriksen (2003) J. Clin. Invest. 112, 440).

A development of further compounds showing a similar effect has been hampered so far by a lack of understanding of the molecular mechanism of the described effects.

Thus, there is a strong need for novel compounds which modulate γ-secretase activity thereby opening new avenues for the treatment of Alzheimer's disease.

The object of the present invention is to provide such compounds.

The object is achieved by a compound having the general formula (I)

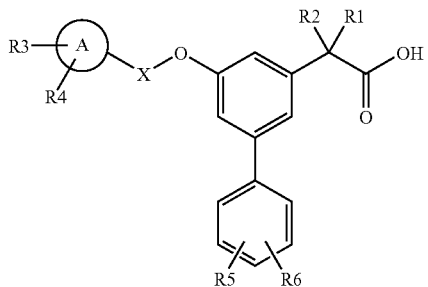

wherein

A is a ring selected from the group consisting of phenyl; $C_{3-7}$ cycloalkyl; and heterocyclyl;

X is a linear $C_1$-$C_4$ alkylene group which is optionally substituted with one or more substituents from the group F, Cl, Br, I and $C_1$-$C_4$ alkyl groups optionally substituted with one or more F, Cl, Br, F;

$R_1$ and $R_2$ are, independently of each other, selected from the group consisting of H; alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; or $R_1$ and $R_2$ being part of a ring, either saturated or unsaturated, having 3 to 6 C-atoms, and which may contain in the ring one or more heteroatoms from the group N, S or O, and which heteroatom may be identical or different if more than one heteroatom is present;

$R_3$, $R_4$, $R_5$ and $R_6$ are independently selected from the group consisting of H; F; Cl; Br; I; CN; OH; $C(O)N(R_7R_8)$; $S(O)_2R_7$; $SO_2N(R_7R_8)$; $S(O)N(R_7R_8)$; $N(R_7)S(O)_2R_8$; $N(R_8)S(O)R_8$; $S(O)_2R_7$; $N(R_7)S(O)_2N(R_8R_{8a})$; $SR_7$; $N(R_7R_8)$; $N(R_7)C(O)R_8$; $N(R_7)C(O)N(R_8R_{8a})$; $N(R_7)C(O)OR_8$; $OC(O)N(R_7R_8)$; $C(O)R_7$; substituted and unsubstituted $C_1$-$C_4$-alkyl and substituted and unsubstituted $C_1$-$C_4$-alkoxy, and wherein the substituents of both groups $C_1$-$C_4$-alkyl and $C_1$-$C_4$-alkoxy are selected from F, Cl, Br, I, $CF_3$;

$R_7$, $R_8$, $R_{8a}$ are independently selected from the group consisting of H; $C_1$-$C_4$-alkyl; heterocyclyl; and $C_{3-7}$ cycloalkyl, wherein $C_1$-$C_4$-alkyl; heterocyclyl; and $C_{3-7}$ cycloalkyl are optionally substituted with one or more substituents independently selected from the group consisting of F, Cl, Br, I and $CF_3$; and/or a salt or ester thereof.

The term "substituted" as used herein includes both part and full substitution. Substituents can be either saturated or unsaturated.

Esters are those according to formula (I) in which H of the carboxyl group is replaced by an organic residue $R_7$. Suitable organic residues are known to a person skilled in the art. Preferred $R_{7a}$ include the following:

An unsubstituted or at least monosubstituted alkyl, preferably a $C_1$-$C_{10}$ alkyl an alkenyl, preferably $C_2$-$C_{10}$-alkenyl, an alkynyl, preferably $C_3$-$C_{10}$-alkynyl, and an unsubstituted or at least monosubstituted, saturated or unsaturated, non-aromatic or aromatic ring having 3 to 6 C-atoms, and which may contain in the ring one or more heteroatoms from the group N, S or O, and which heteroatom may be identical or different if more than one heteroatom is present. Said substituents being selected from the group consisting of halogen, alkyl, alkenyl, alkynyl, N, S, O, carboxyl, sulphonyl, and the like and which can be flier substituted.

Examples for current aromatic groups include aryl groups, for example phenyl groups, and heteroaryl groups, which aryl and heteroaryl groups may be substituted, preferably by the substituents given above.

The term "$C_1$-$C_4$-alkyl" refers to methyl, ethyl, n-propyl, iso-propyl, n-butyl, iso-butyl and tert.-butyl.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Heterocyclyl" or "heterocycle" means a cyclopentane, cyclohexane or cycloheptane ring that may contain up to the maximum number of double bonds (aromatic or non-aromatic ring which is fully, partially or un-saturated) wherein at least one carbon atom up to 4 carbon atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a heterocycle include but are not restricted to furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, azepine or homopiperazine. "Heterocycle" means also azetidine.

In preferred embodiments, the invention relates to a compound having the general formula (I) wherein A; X; $R_1$ and $R_2$; and $R_3$, $R_4$, $R_5$ and $R_6$ independently of each other have the following meanings:

A is phenyl; cyclopropyl; cyclohexyl; or a 6-membered aromatic heterocycle.

X is a $CH_2$ group which is optionally substituted with one or more substituents from the group F, Cl, Br, I and $C_1$-$C_4$ alkyl groups optionally substituted with one or more F, Cl, Br, I; and/or $R_1$ and $R_2$ being H; or $R_1$ being H and $R_2$ being $CH_3$, $C_2H_5$, $C_3H_7$ or $C_4H_9$ or isomers thereof: or $R_1$ and $R_2$ being $CH_3$ or $R_1$, $R_2$ jointly form together with the carbon atom to which they are attached a cyclopropyl ring; and/or $R_3$, $R_4$, $R_5$ and $R_6$ are independently selected from the group consisting of H; OH; $C_1$-$C_4$-alkyl or $C_1$-$C_4$-alkoxy, substituted partly or fully by F, Cl, Br, I; C(O)NH$_2$, S(O)$_2$C$_1$-C$_4$-alkyl, S(O)$_2$-heterocyclyl;

and/or a salt or ester thereof.

Within this group) of embodiments, it is even more preferred if all the groups A; X; $R_1$ and $R_2$; and $R_3$, $R_4$, $R_5$ and $R_6$ have the meanings defined beforehand.

It is more preferred if A; X; $R_1$ and $R_2$; and $R_3$, $R_4$, $R_5$ and $R_6$ independently of each other have the following meanings:
A is phenyl; and/or
X is $CH_2$ or $CHCH_3$; and/or
$R_1$ and $R_2$ being H; or $R_1$ being H and $R_2$ being $CH_3$, $C_2H_5$, $C_3H_7$ or $C_4H_9$ or isomers thereof, or $R_1$ and $R_2$ being $CH_3$ or $R_1$, $R_2$ jointly form together with the carbon atom to which they are attached a cyclopropyl ring; and/or $R_3$, $R_4$, $R_5$ and $R_6$ are independently selected from the group consisting of H, OH, $CH_3$, $OCH_3$, $CF_3$, $OCF_3$, C(O)NH$_2$, S(O)$_2$—$C_1$-$C_4$-alkyl, S(O)$_2$-heterocyclyl, F, and Cl;

and/or a salt or ester thereof.

Within this group of embodiments, it is even more preferred if all the groups A; X; $R_1$ and $R_2$; and $R_3$, $R_4$, $R_5$ and $R_6$ have the meanings defined beforehand.

In an even more preferred embodiment, the invention relates to compounds selected from the group consisting of
I) [5-(4-Fluoro-benzyloxy)-4'-trifluoromethyl-biphenyl-3-yl]-acetic acid;
II) [5-(4-Isopropyl-benzyloxy)-4'-trifluoromethyl-biphenyl-3-yl]-acetic acid;
III) [4'-Trifluoromethyl-5-(4-trifluoromethyl-benzyloxy)-biphenyl-3-yl]-acetic acid;
IV) [5-(4-Methanesulfonyl-benzyloxy)-4'-trifluoromethyl-biphenyl-3-yl]-acetic acid;
V) (5-Cyclohexylmethoxy-4'-trifluoromethyl-biphenyl-3-yl)-acetic acid;
VI) {5-[4-(Pyrrolidine-1-sulfonyl)-benzyloxy]-4'-trifluoromethyl-biphenyl-3-yl}-acetic acid;
VII) (5-Benzyloxy-biphenyl-3-yl)-acetic acid;
VIII) 2-(5-Benzyloxy-4'-trifluoromethyl-biphenyl-3-yl)-pentanoic acid;
IX) (5-Benzyloxy-3',5'-dichloro-biphenyl-3-yl)-acetic acid;
X) 5-Benzyloxy)-4'-trifluoromethyl-biphenyl-3-yl)-acetic acid;
XI) (5-Benzyloxy-3',5'-bis-trifluoromethyl-biphenyl-3-yl)-acetic acid;
XII) (5-Benzyloxy-3',4'-dichloro-biphenyl-3-yl)-acetic acid;
XIII) (5-Benzyloxy-4'-trifluoromethoxy-biphenyl-3-yl)-acetic acid;
XV) (5-Benzyloxy-3'-methoxy-biphenyl-3-yl)-acetic acid;
XV) (5-Benzyloxy-3'-carbamoyl-biphenyl-3-yl)-acetic acid;
XVI) (5-Benzyloxy-3'-hydroxy-biphenyl-3-yl)-acetic acid,
XVI) (5-Benzyloxy-4'-methanesulfonyl-biphenyl-3-yl)-acetic acid;
(5-Benzyloxy-4'-sulfamoyl-biphenyl-3-yl)-acetic acid;
XIX) 2-(5-Benzyloxy-4'-trifluoromethyl-biphenyl-3-yl)-propionic acid;
XX)-2-(5-Benzyloxy-4'-trifluoromethyl-biphenyl-3-yl)-2-methyl-propionic acid;
XXI) 1-(5-Benzyloxy-4'-trifluoromethyl-biphenyl-3-yl)-cyclopropanecarboxylic acid;
XXII) (5-Benzyloxy-4'-fluoro-biphenyl-3-yl)-acetic acid;
XXIII) (5-Benzyloxy-4'-chloro-biphenyl-3-yl)-acetic acid,
XXIV) (4'-Acetylamino-5-benzyloxy-biphenyl-3-yl)-acetic acid;
XXV) (5-Benzyloxy-4'-hydroxy-biphenyl-3-yl)-acetic acid;
XXVI) (5-Benzyloxy-4'-isopropoxy-biphenyl-3-yl)-acetic acid;
XXVII)(5-Benzyloxy-3',5'-difluoro-biphenyl-3-yl)-acetic acid;
XXIII) (5-Benzyloxy-3'-isopropoxy-biphenyl-3-yl)-acetic acid;
XXIX) (5-Benzyloxy-4'-methoxy-biphenyl-3-yl)-acetic acid;
XXX) (5-Benzyloxy-2'-methoxy-biphenyl-3-yl)-acetic acid;
XXXI) (5-Benzyloxy-2'-methyl-biphenyl-3-yl)acetic acid;
XXXII) (5-Benzyloxy-3'-methyl-biphenyl-3-yl)-acetic acid;
XXXIII) (5-Benzyloxy-3'-trifluoromethyl-biphenyl-3-yl)-acetic acid;
XXXIV) (5-Benzyloxy-2'-fluoro-biphenyl-3-yl)-acetic acid;
XXXV) (5-Benzyloxy-4'-methyl-biphenyl-3-yl)-acetic acid;
XXXVI) (5-Benzyloxy-3'-fluoro-biphenyl-3-yl)-acetic acid;

XXVII) (5-Benzyloxy-3'-chloro-biphenyl-3-yl)-acetic acid;
XXXVIII) (5-Benzyloxy-3'-trifluoromethoxy-biphenyl-3-yl)-acetic acid;
XXXIX) 2-{5-[4-(Pyrrolidine-1-sulfonyl)-benzyloxy]-4'-trifluoromethyl-biphenyl-3-yl}-pentanoic acid;
XL) 2-(5-Cyclopropylmethoxy-4'-trifluoromethyl-biphenyl-3-yl)-pentanoic acid;
XLI) [5-(4-Chloro-benzyloxy)-4'-trifluoromethyl-biphenyl-3-yl]-acetic acid;
XLII) (5-Cyclopropylmethoxy-4'-trifluoromethyl-biphenyl-3-yl)-acetic acid;
XLIII) [5-(5-Methyl-isoxazol-3-ylmethoxy)-4'-trifluoromethyl-biphenyl-3-yl]-acetic acid;
XLIV) [5-(3,5-Dichloro-benzyloxy)-4'-trifluoromethyl-biphenyl-3-yl]-acetic acid;
XLV) [5-(Tetrahydro-pyran-4-ylmethoxy)-4'-trifluoromethyl-biphenyl-3-yl]-acetic acid;
XLVI) [5-(4-Dimethylsulfamoyl-benzyloxy)-4'-trifluoromethyl-biphenyl-3-yl]-acetic acid;
XLVII) [5-(1-Phenyl-ethoxy)-4'-trifluoromethyl-biphenyl-3-yl]-acetic acid;
XLVIII) {5-[4-(Morpholine-4-carbonyl)-benzyloxy]-4'-trifluoromethyl-biphenyl-3-yl}-acetic acid;
XLIX) [4'-Trifluoromethyl-5-(3-trifluoromethyl-benzyloxy)-biphenyl-3-yl]-acetic acid,
L) [4'-Trifluoromethyl-5-(2-trifluoromethyl-benzyloxy)-biphenyl-3-yl]-acetic acid,
LI) (5-Phenethyloxy-4'-trifluoromethyl-biphenyl-3-yl)-acetic acid;
LII) [5-(Tetrahydro-pyran-2-ylmethoxy)-4'-trifluoromethyl-biphenyl-3-yl]-acetic acid,
LIII) [5-(4-Dimethylcarbamoyl-benzyloxy)-4'-trifluoromethyl-biphenyl-3-yl]-acetic acid;
LIV) [5-(4-Methylcarbamoyl-benzyloxy)-4'-trifluoromethyl-biphenyl-3-yl]-acetic acid;
LV) {5-[4-(Pyrrolidine-1-carbonyl)-benzyloxy]-4'-trifluoromethyl-biphenyl-3-yl}-acetic acid;
LVI) {5-[4-(Morpholine-4-sulfonyl)-benzyloxy]-4'-trifluoromethyl-biphenyl-3-yl}-acetic acid;
LVII) [5-(4-Trifluoromethoxy-benzyloxy)-4'-trifluoromethyl-biphenyl-3-yl]-acetic acid;
LVIII) [5-(2-Chloro-benzyloxy)-4'-trifluoromethyl-biphenyl-3-yl]-acetic acid;
LIX) [5-(3-Chloro-benzyloxy)-4'-trifluoromethyl-biphenyl-3-yl]-acetic acid,
LX) [5-(4-Methyl-benzyloxy)-4'-trifluoromethyl-biphenyl-3-yl]-acetic acid;
LXI) 2-(5-Benzyloxy-4'-trifluoromethyl-biphenyl-3-yl)-pent-4-enoic acid,
LXII) (R)-2-(5-Cyclopropylmethoxy-4'-trifluoromethyl-biphenyl-3-yl)pentanoic acid;
LXIII) (S)-2-(5-Cyclopropylmethoxy-4'-trifluoromethyl-biphenyl-3-yl)-pentanoic acid;
LXIV) R)-2-(5-Benzyloxy-4'-trifluoromethyl-biphenyl-3-yl)-pentanoic acid;
LXV) (S)-2-(5-Benzyloxy-4'-trifluoromethyl-biphenyl-3-yl)-pentanoic acid;

and/or a salt or ester thereof.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

Compounds according to the invention which contain one or more basic groups, i.e. groups which can be protonated, can be used according to the invention in the form of their addition salts with inorganic or organic acids.

Examples for suitable acids include hydrogen chloride, hydrogen bromide; phosphoric acid, sulfuric acid, nitric acid, methanesulfonic acid, p-toluenesulfonic acid, napthalenedisulfonic acid, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person skilled in the art.

The term "pharmaceutically acceptable" means approved by a regulatory agency such as the EMEA (Europe) and/or the FDA (US) and/or any other national regulatory agency for use in animals, preferably in humans.

Compounds according to the invention which contain several basic groups can simultaneously form different salts.

If a compound according to the invention simultaneously contains acidic and basic groups in the molecule, the invention also includes, in addition to the salt forms mentioned, inner salts or betaines.

The respective salts of the compounds according to the invention can be obtained by customary methods which are known to the person skilled in the art, for example by contacting these with an organic or inorganic acid or base in a solvent or dispersant, or by anion exchange or cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according of the invention in any suitable manner, such as any suitable in vitro assay.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds's according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The compounds according to general formula (I) can be prepared according to methods published in the literature or by analogous methods.

Methods for synthesis of the compounds are described e.g., in Houben-Weyl, Methoden der Organischen Chemie (Methods of Organic Chemistry), Thieme-Verlag, Stuttgart, and Organic Reactions, John Wiley & Sons, New York.

Depending on the circumstances of the individual case, in order to avoid side reactions during the synthesis of a compound of the general formula (I), it can be necessary or advantageous to temporarily block functional groups by introducing protective groups and to deprotect them in a later stage of the synthesis, or to introduce functional groups in the form of precursor groups and at a later stage to convert them into the desired functional groups. Suitable synthetic strategies, protective groups and precursor groups are known to the person skilled in the art.

If desired, the compounds of the formula (I) can be purified by customary purification procedures, for example by recrystallization or chromatography. The starting materials for the preparation of the compounds of the formula (I) are commercially available or can be prepared according to or analogously to literature procedures.

These can serve as a basis for the preparation of the other compounds according to the invention by several methods well known to the person skilled in the art.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced.

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129).

With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 µM.

Such a γ-secretase modulation can be carried out, e.g. in animals such as mammals. Exemplary mammals are mice, rats, guinea pigs, monkeys, dogs, cats. The modulation can also be carried out in humans.

In a particular embodiment of the invention, said modulation is performed in vitro or in cell culture.

As known to the person skilled in the art, several in vitro and cell culture assays are available.

An example for such an assay is described in WO-03/008635.

Concentrations of the various products of the γ-secretase cleavage (the Aβ-peptides) can be determined by various methods known to a person skilled in the art. Examples for such methods include determination of the peptides by mass-spectrometry or detection by antibodies.

Suitable antibodies are available for example from The Genetics Company, Inc., Switzerland.

Further information is disclosed for example in N. Ida et al. (1996) J. Biol. Chem. 271, 22908, and M. Jensen et al. (2000) Mol. Med. 6, 291. Antibody-based kits are also available from Innogenetics, Belgium.

Cells which can be employed in such assays include cells which physiologically express the γ-secretase complex and cells which transiently or stably express some or all interactors of the γ-secretase complex.

Numerous available cell lines suitable for such assays are known to the skilled person Cells and cell lines of neuronal or glial origin are particularly suitable. Furthermore, cells and tissues of the brain as well as homogenates and membrane preparations thereof may be used.

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The invention further relates to the use of said compounds for the preparation of a medicament for the modulation of γ-secretase activity.

The activity of the γ-secretase can be modulated in different ways, i.e. resulting in different profiles of the various Aβ-peptide.

Uses of a compound for the modulation of γ-secretase activity resulting in a decrease in the relative amount of Aβ42-protein produced are preferred.

Respective dosages, routes of administration, formulations etc are disclosed further below.

The invention further relates to the use of the compounds according to the invention for the treatment of a disease associated with an elevated level of Aβ42-production.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type/non-pathological situation.

As outlined above, such an elevated Aβ42-level is a hallmark of patients developing or suffering from Alzheimer's disease.

Furthermore the invention relates to a composition comprising a compound according to the invention in a mix-tire with an inert carrier.

In a preferred embodiment, the invention relates to a composition comprising a compound according to the invention in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Furthermore, the invention relates to a method for the preparation of a compound according to the invention comprising the steps of coupling a phenyl acetic acid derivative, optionally said derivative being protected, with an appropriate aromatic compound and optional further functionalisation and deprotection of the thus-obtained biphenyl compound.

In one embodiment a dihydroxyphenylacetic acid derivative can be alkylated with a benzyl halide, typically a benzyl bromide, using an inorganic base such as an alkali metal carbonate, typically potassium carbonate in a suitable solvent such as acetonitrile. The resultant alcohol can be converted to a triflate using eg trifluoromethanesulphonic anhydride, an organic base such as pyridine and in a suitable solvent such as dichloromethane. This triflate can then be coupled to a boronic acid under the variety of conditions known to those skilled in the art for such Suzuki coupling, typically using a solvent such as 1,2-dimethoxyethane, an alkali metal halide such as caesium fluoride, ad a palladium compound such as tetrakis(triphenylphoshine)palladium (0).

Optionally the method for the preparation of a compound according to the present invention further comprises the step of reacting the biphenyl compound with an appropriate halide or di-halide to result in a compound according to the present invention, wherein at least one of $R_1$, $R_2$ is other than H.

Conversion of the ester to the acid can be done using a base such as an alkali metal hydroxide, typically lithium hydroxide, in the presence of water and other suitable solvents such as tetrahydrofuran and methanol.

In another embodiment for the preparation of a compound according to the present invention, a dibromofluorobenzene can be treated with a benzyl alcohol in the presence of an alkali metal hydride, typically sodium hydride, in a suitable aprotic solvent such as tetrahydrofuran. The product can be treated with a suitable malonic acid derivative, such as malonic acid tert-butyl ester ethyl ester in the presence of an alkali metal hydride, typically sodium hydride and a metal halide, typically a copper halide, preferably copper bromide. Further treatment in an acidic solvent such as acetic acid at elevated temperature provides a benzyloxy-bromophenylacetic acid ester. This can be coupled to a boronic acid under the variety of conditions known to those skilled in the art for such Suzuki coupling, typically using solvents such as 1,2-dimethoxyethane and water, an alkali metal carbonate such as potassium carbonate, and a palladium compound such as tetrakis(triphenylphosphine)palladium (0).

Conversion of the ester to the acid can be done using a base such as an alkali metal hydroxide, typically lithium hydroxide in the presence of water and other suitable solvents such as tetrahydrofuran and methanol.

If required the biphenyl carboxylic acid can be alkylated by treatment in a suitable aprotic solvent such as tetrahydrofuran with a suitable base such as a metal hexamethyldisilazide, typically LiHMDS, and the appropriate halide at a suitable temperature, typically −15° C.

In another embodiment such a group can be incorporated by treating the ester in a suitable solvent such as DMF with a suitable base such as an alkali metal hydride, typically sodium hydride at a suitable temperature, such as −4° C., and with the appropriate halide.

Conversion of the ester to the acid can be done using a base such as an alkali metal hydroxide, typically lithium hydroxide in the presence of water and other suitable solvents such as tetrahydrofuran and methanol.

Furthermore, the invention relates to a method for the preparation of a medicament comprising the steps of:
a) preparing a compound according to the invention
b) formulation of a medicament containing said compound.

The compounds according to the invention and their pharmaceutically acceptable salts, optionally in combination with other pharmaceutically active compounds suitable to treat or prevent Alzheimer's disease such as Aricept (Eisai), Donepezil (Pfizer), Cognex (Warner-Lambert). Tacrine (Warner-Lambert), Axura (Merz), Memantine (Merz) or with any other of the drugs known to a person skilled in the art suitable to treat or prevent Alzheimer's disease, can be administered to animals, preferably to mammals, and in particular humans, as pharmaceuticals by themselves, in mixtures with one another or in the form of pharmaceutical preparations.

Various delivery systems are known and can be used to administer a compound of the invention for the treatment of Alzheimer's disease/for the modulation of the γ-secretase activity, e.g. encapsulation in liposomes, microparticles, and microcapsules:

If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In another embodiment, the compound can be delivered in a vesicle, in particular a liposome (Langer (1990) Science 249, 1527; Treat et al. (1989) Liposomes in the Therapy of Infectious Disease and Cancer, Lopez-Berestein and Fidler, eds., Liss, New York, 353; Lopez-Berestein, ibid., 317)

In yet another embodiment, the compound can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Medical Applications of Controlled Release, Langer and Wise, eds., CRC Press, Boca Raton, Fla. (1974); Controlled Drug Bioavailability, Drug Product Design and Performance, Smolen and Ball, eds., Wiley, New York (1984); Ranger and Peppas (1983) Macromol. Sci. Rev. Macromol. Chem. 23, 61; Levy et al. (1985) Science 228, 190; During et al. (1989) Ann. Neurol. 25, 351; Howard et al; (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active, compound per kilogram body weight. Suitable dosage ranges for intranasal administration are generally about 0.01 mg/kg body weight to 1 mg/kg body weight Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Iry et al. (1997) J. Neuropathol. Exp. Neurol. 56, 965; Lehman et al. (2003) Neurobiol. Aging 24, 645.

Substantial data from several studies are available to the skilled person in the art which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest 112, 440; Yan et al. (2003) J Neurosci. 23, 7504;

General

All reactions were carried out under inert atmosphere. NMR spectra were obtained on a Bruker dpx400. LCMS was carried out on an Agilent 1100 using a ZORBAX® SB-C18, 4.6×150 mm, 5 micron column for methods A and B and a ZORBAX® SB-C18, 4.6×75 mm, 3.5 micron column for method C. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
|---|---|---|
| A | 1 ml/min | 0-1.5 min 5-95% MeCN |
| | | 1.5-6 min 95% MeCN |
| | | 6-6.5 min 95%-5% MeCN |
| B | 1 ml/min | 0-11 min 5-95% MeCN |
| | | 11-13 min 95% MeCN |
| | | 13-14 min 95%-5% MeCN |
| C | 1 ml/min | 0-1.5 min 30-95% MeCN |
| | | 1.5-4.5 min 95% |
| | | 4.5-5 min 95%-5% MeCN |

Abbreviations

| | |
|---|---|
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| eq | Equivalents |
| Et | Ethyl |
| EtOAc | ethyl acetate |
| g | Gram |
| h | Hour |
| HPLC | high pressure liquid chromatography |
| $K_2CO_3$ | Potassium carbonate |
| l | Litre |

-continued

| | |
|---|---|
| LCMS | liquid chromatography - mass spectrometry |
| LDA | lithium diisopropylamide |
| M | Molar |
| m | Multiplet |
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

EXAMPLES

Example 1

Preparation of [5-(4-fluoro-benzyloxy)-4'-trifluoromethyl-biphenyl-3-yl]-acetic Acid (I)

(3,5-Dihydroxy-phenyl)-acetic acid methyl ester (0.500 g, 2.75 mmol) in MeCN (5 ml) was treated with $K_2CO_3$ (0.095 g, 6.88 mmol) and 4-fluorobenzyl bromide (0.520 g, 2.75 mmol). The resultant mixture was stirred overnight at room temperature. The reaction mixture was directly purified by flash column chromatography (EtOAc:iso-hexane) to give [3-(4-fluoro-benzyloxy)-5-hydroxy-phenyl]-acetic acid methyl ester (0.15 g).

[3-(4-Fluoro-benzyloxy)-5-hydroxy-phenyl]-acetic acid methyl ester (0.14 g) in DCM (5 ml) was treated with pyridine (116 µl, 1.44 mmol) and trifluoromethanesulfonic anhydride (0.16 g, 0.58 mmol) was added dropwise. The mixture was stirred for 3 h at room temperature. The mixture was diluted with further DCM, washed with HCl solution (IM aq), dried ($MgSO_4$) and concentrated under vacuum to give [3-(4-fluoro-benzyloxy)-5-trifluoromethanesulfonyloxy-phenyl]-acetic acid methyl ester as an orange-brown oil (0.16 g).

[3-(4-Fluoro-benzyloxy)-5-trifluoromethanesulfonyloxy-phenyl]-acetic acid methyl ester (0.15 g) was combined in DME (4 ml) with CsF (0.13 g, 0.83 mmol), 4-trifluoromethylbenzeneboronic acid (0.086 g, 6.45 mmol) and tetrakis(triphenylphoshine)palladium(0) (0.013 g, 0.011 mmol). The mixture was heated to 90° C. for 10 min in a CEM microwave. The mixture was diluted with EtOAc, washed with water and $NaHCO_3$ solution (sat aq), dried ($MgSO_4$) and concentrated under vacuum. The residue was purified by flash column chromatography (EtOAc:iso-hexane) to give 5-(4-fluoro-benzyloxy)-4'-trifluoromethyl-biphenyl-3-yl]-acetic acid methyl ester (0.035 g) as a white solid.

5-(4-Fluoro-benzyloxy)-4'-trifluoromethyl-biphenyl-3-yl]-acetic acid methyl ester (0.035 g) in THF (2 ml) was treated with LiOH solution (210 ul, 1M aq) and a few drops of MeOH. The mixture was stirred at room temperature for 2 h and then diluted with water, acidified with HCl solution (2M aq) and extracted with EtOAc (×3). The extracts were combined, dried ($MgSO_4$) and concentrated under vacuum. The crude product was purified by preparative HPLC to give 5-(4-fluoro-benzyloxy)-4'-trifluoromethyl-biphenyl-3-yl]-acetic acid as a white solid (0.012 g, 0.03 mmol). $^1H$ NMR ($CDCl_3$) δ 7.65 (q, 4H), 7.41 (q, 2H) 7.07 (m, 4H), 6.94 (s, 1H), 5.06 (s, 2H), 3.68 (s, 2H); LCMS method (A), 5.2 min.

Example 2

Screening of the Compounds of the Invention for γ-Secretase-Modulating Activity

Screening was carried out using SKN neuroblastoma cells carrying the APP-"swedish mutant" (point mutations at position 595 and 596, numbering based on APP695) grown in DMEM/NUT-mix F12 (HAM) provided by Gibco (cat no. 31330-38) containing 5% Serum/Fe supplemented with 1% non-essential amino acids, 100 U/ml Pen/Strep.

Cells were grown to near confluency.

The screening was performed using the assay as described in Citron et al (1997) Nature Medicine 3: 67.

$IC_{50}$-Values of Selected Compounds of the Invention on the γ-Secretase Activity.

Activity Ranges: A=<1 uM; B=1-10 uM; C=10-100 uM; D=100-300 uM.

| Compound No | Activity range |
|---|---|
| I) | B |
| II) | B |
| III) | A |
| IV) | C |
| V) | A |
| VI) | B |
| VII) | B |
| VIII) | A |
| IX) | B |
| X) | B |
| XI | B |
| XII | B |
| XIII | B |
| XIV | C |
| XV | C |
| XVI | C |
| XVII | C |
| XVIII | C |
| XIX | B |
| XX | B |
| XXI | B |
| XXII | C |
| XXIII | B |
| XXIV | D |
| XXV | D |
| XXVI | C |
| XXVII | C |
| XXVIII | C |
| XXIX | C |
| XXX | C |
| XXXI | C |
| XXXII) | C |
| XXXIII) | C |
| XXXIV) | C |
| XXXV | C |
| XXXVI | C |
| XXXVII | D |
| XXXVIII | B |
| XXXIX | B |
| XL | B |
| XLI | B |
| XLII | B |
| XLIII | C |
| XLIV | B |
| XLV) | C |
| XLVI | B |
| XLVII | B |
| XLVIII | C |
| XLIX | B |

-continued

| Compound No | Activity range |
|---|---|
| L | B |
| LI | B |
| LII | D |
| LIII | D |
| LIV | D |
| LV | C |
| LVI | C |
| LVII | B |
| LVIII | B |
| LIX | B |
| LX | B |

Example 3

Determination of the Effect of the Compounds According to the Invention on Cyclooxygenase-1 and Cyclooxygenase-2 (Cox-1, Cox-2)

Inhibition of Cox-1 and Cox-2 was determined using the Colorimetric Cox inhibitor screening assay provided by Cayman Chemical Company, Ann Arbor, Mich., USA. (Cat. No. 760111) according to manufacturer's instructions.

The following compounds show <50% inhibition at 100 uM:

[5-(4-Fluoro-benzyloxy)-4'-trifluoromethyl-biphenyl-3-yl]-acetic acid;

[4'-Trifluoromethyl-5-(4-trifluoromethyl-benzyloxy)-biphenyl-3-yl]-acetic acid;

(5-Cyclohexylmethoxy-4'-trifluoromethyl-biphenyl-3-yl)-acetic acid;

{5-[4-(Pyrrolidine-1-sulfonyl)-benzyloxy]-4'-trifluoromethyl-biphenyl-3-yl}-acetic acid;

2-(5-Benzyloxy-4'-trifluoromethyl-biphenyl-3-yl)-pentanoic acid;

(5-Benzyloxy-3',5'-dichloro-biphenyl-3-yl)-acetic acid;

5-Benzyloxy-4'-trifluoromethyl-biphenyl-3-yl)acetic acid;

(5-Benzyloxy-4'-trifluoromethoxy-biphenyl-3-yl)-acetic acid;

2-(5-Benzyloxy-4'-trifluoromethyl-biphenyl-3-yl)-propionic acid;

2-(5-Benzyloxy-4'-trifluoromethyl-biphenyl-3-yl)-2-methyl-propionic acid;

1-(5-Benzyloxy-4'-trifluoromethyl-biphenyl-3-yl)-cyclopropanecarboxylic acid;

2-{5-[4-(Pyrrolidine-1-sulfonyl)-benzyloxy]-4'-trifluoromethyl-biphenyl-3-yl}-pentanoic acid;

2-(5-Cyclopropylmethoxy-4'-trifluoromethyl-biphenyl-3-yl)-pentanoic acid;

(5-Cyclopropylmethoxy-4'-trifluoromethyl-biphenyl-3-yl)-acetic acid;

[5-(3,5-Dichloro-benzyloxy)-4'-trifluoromethyl-biphenyl-3-yl]-acetic acid;

[5-(4-Dimethylsulfamoyl-benzyloxy)-4'-trifluoromethyl-biphenyl-3-yl]-acetic acid;

[5-(1-Phenyl-ethoxy)-4'-trifluoromethyl-biphenyl-3-yl]-acetic acid.

Example 4

Preparation of [5-(4-isopropyl-benzyloxy)-4'-trifluoromethyl-biphenyl-3-yl]-acetic Acid (II)

Procedure as for example 1 replacing 4-fluorobenzyl bromide with 4-isopropylbenzyl bromide. $^1$H NMR (CDCl$_3$) δ 7.66 (m, 4H), 7.38 (d, 2H), 7.27 (d, 2H), 7.13 (s, 1H), 7.11 (s, 1H), 6.97 (s, 1H), 5.07 (s, 2H), 3.70 (s, 2H), 2.93 (m, 1H), 1.26 (d, 6H); LCMS method (A), RT=5.0 min.

Example 5

Preparation of [4'-trifluoromethyl-5-(4-trifluoromethyl-benzyloxy)-biphenyl-3-yl]-acetic Acid (II)

Procedure as for example 1 replacing 4-fluorobenzyl bromide with 4-trifluoromethylbenzyl bromide. $^1$H NMR (CDCl$_3$) δ 7.60-7.70 (m, 6H), 7.56 (d, 2H), 7.12 (s, 1H), 7.11 (s, 1H), 6.95 (s, 1H), 5.17 (s, 2H), 3.70 (s, 2H); LCMS method (A), RT=4.5 min.

Example 6

Preparation of [5-(4-methanesulfonyl-benzyloxy)-4'-trifluoromethyl-biphenyl-3-yl]-acetic Acid (IV)

Procedure as for example 1 replacing 4-fluorobenzyl bromide with 1-bromomethyl-4-methanesulfonyl-benzene. $^1$H NMR (CDCl$_3$) δ 7.93 (d, 2H), 7.55-7.65 (m, 6H), 7.11 (s, 1H), 7.04 (s, 1H), 6.93 (s, 1H), 5.17 (s, 2H), 3.60 (s, 2H), 3.03 (s, 3H); LCMS method (A), (M-H$^-$) 462.9, RT=3.9 min.

Example 7

Preparation of (5-cyclohexylmethoxy-4'-trifluoromethyl-biphenyl-3-yl)acetic Acid (V)

Procedure as for example 1 replacing 4-fluorobenzyl bromide with bromomethyl-cyclohexane. $^1$H NMR (CDCl$_3$) δ 7.67 (s, 4H), 7.07 (s, 1H), 7.03 (s, 1H), 6.86 (s, 1H), 3.78 (d, 2H), 3.69 (s, 2H), 1.80-167 (m, 6H), 1.38-1.15 (m, 3H), 1.14-1.00 (m, 2H); LCMS method (A), RT=5.5 min.

Example 8

Preparation of {5-[4-(Pyrrolidine-1-sulfonyl)-benzyloxy]-4'-trifluoromethyl-biphenyl-3-yl}-acetic Acid (VI)

Procedure as for example 1 replacing 4-fluorobenzyl bromide with 4-(pyrrolidine-1-sulfonyl)-benzyl bromide. $^1$H NMR (CDCl$_3$) δ 7.85 (d, 2H), 7.58-7.72 (m, 6H), 7.14 (s, 1H), 7.11 (s, 1H), 6.96 (s, 1H), 5.19 (s, 2H), 3.71 (s, 2H), 3.20-3.30 (m, 4H), 1.70-1.80 (m, 4H); LCMS method (A), RT=4.2 min.

Example 9

Preparation of (5-benzyloxy-biphenyl-3-yl)-acetic Acid (VII)

Preparation or 1-benzyloxy-3,5-dibromobenzene

Benzylalcohol (9.7 ml, 94 mmol) was added dropwise to a suspension of NaH (4.0 g of a 60% suspension in mineral oil, 100 mmol) in THF (150 ml) at room temperature and the mixture was stirred at room temperature for 1 h before 1,3-dibromo-5-fluorobenzene (15.9 g, 62.5 mmol) was added.

The reaction was stirred at room temperature for 12 h. Water was added carefully and the THF was evaporated under reduced pressure. The residue was extracted with iso-hexane (×3) and the combined organic extracts were washed with NaOH solution (1M aq). water, brine, dried (MgSO$_4$), filtered and concentrated under reduced pressure. The residue was purified by flash column chromatography (EtOAc:petroleum ether) to give 1-benzyloxy-3,5-dibromobenzene (14.7 g, 65 mmol) as a colourless liquid in 69% yield. $^1$H NMR (CDCl$_3$) δ 7.45-7.33 (m, 5H), 7.30-7.28 (m, 1H), 7.10-7.08 (m, 2H), 5.02 (s, 2H).

Preparation of (3-benzyloxy-5-bromo-phenyl)-acetic Acid Ethyl Ester

Malonic acid tert-butyl ester ethyl ester (10.2 ml, 53.8 mmol) was added dropwise to a suspension of NaH (2.2 g of a 60% suspension in mineral oil, 53.8 mmol) in dioxane (200 ml) at room temperature and the mixture was stirred at this temperature for 1 h before CuBr (7.7 g, 53.5 mmol) and 1-benzyloxy-3,5-dibromobenzene (9.2 g, 26.9 mmol) were added. The reaction mixture was heated to reflux for 5 h. HCl solution (1M aq, 100 ml) was carefully added and the mixture was extracted with a iso-hexane (×3). The combined organic extracts were washed with HCl solution (IM aq), water, brine, dried (MgSO$_4$), filtered and concentrated under reduced pressure. The residue was purified by flash column chromatography (EtOAc:petroleum ether) to give, in order of elution, recovered 1-benzyloxy-3,5-dibromobenzene (3.2 g, 9.4 mmol) in 35% yield and 2-(3-benzyloxy-5-bromo-phenyl)-malonic acid tert-butyl ester ethyl ester (7.2 g, contains 1.4 equivalent malonic acid tert-butyl ester ethyl ester, 10 mmol) as a colourless liquid in 37% yield.

2-(3-Benzyloxy-5-bromophenyl)malonic acid tert-butyl ester ethyl ester (7.2 g, contains 1.4 equivalent malonic acid tert-butyl ester ethyl ester, 10 mmol) was dissolved in glacial AcOH (50 ml) and heated to reflux for 12 h. The AcOH was removed under reduced pressure. The residue was poured into Na$_2$CO$_3$ solution (sat aq) and the mixture was extracted with EtOAc (×3). The combined organic extracts were washed with water, brine, dried (MgSO$_4$), filtered and concentrated under reduced pressure to give (3-benzyloxy-5-bromo-phenyl-)acetic acid ethyl ester (6.8 g, 9.7 mmol) as a yellow liquid in 97% yield. $^1$H NMR (CDCl$_3$) δ 7.44-7.30 (m, 5H), 7.07-7.03 (m, 2H), 6.87-6.84 (m, 1H), 5.03 (s, 2H), 4.15 (q, 2H), 3.54 (s, 2H), 1.26 (t, 3H).

Preparation of (5-benzyloxy-biphenyl-3-yl)-acetic Acid Ethyl Ester (3-Benzyloxy-5-bromophenyl)-acetic acid ethyl ester (0.250 g, 0.72 mmol), benzene boronic acid (0.10 g, 0.86 mmol) and tetrakis(triphenylphosphine)palladium(0) (0.04 g, 0.04 mmol) were suspended in a mixture of K$_2$CO$_3$ solution (0.72 ml, 1.44 mmol, 2M aq) and DME (2 ml). This reaction mixture was irradiated in a CEM microwave at 120° C. for 30 min. The reaction mixture was diluted with water and extracted with Et$_2$O (×3). The combined organic extracts were washed with water, dried (MgSO$_4$), filtered and concentrated under reduced pressure. The residue was purified by flash column chromatography (EtOAc:petroleum ether) to give (5-benzyloxy-biphenyl-3-yl)-acetic acid ethyl ester (0.12 g, 0.35 mmol) as a colourless gum in 48% yield. $^1$H NMR (CDCl$_3$) δ 7.59-7.54 (m, 2H), 7.48-7.30 (m, 8H), 7.13-7.11 (m, 2H), 6.94-6.91 (m, 1H), 5.12 (s, 2H), 4.16 (q, 2H), 3.64 (s, 2H), 1.27 (t, 3H).

Preparation of (5-benzyloxy-biphenyl-3-yl)-acetic Acid

NaOH solution (1 ml, 1M aq) was added to a solution of (5-benzyloxy-biphenyl-3-yl)acetic acid ethyl ester (0.12 g, 0.35 mmol) in EtOH (2 ml) and the mixture was stirred at room temperature for 12 h. The reaction mixture was diluted with HCl solution (2M aq) and extracted with EtOAc (×3). The combined organic extracts were washed with water, brine, dried (MgSO$_4$), filtered and concentrated under reduced pressure to give (5-benzyloxybiphenyl-3-yl)acetic acid (0.12 g, 0.31 mmol) as colourless solid in 90% yield. $^1$H NMR (CDCl$_3$) δ 7.57-7.56 (m, 2H), 7.48-7.30 (m, 8H), 7.15-7.10 (m, 2H), 6.94-6.90 (m, 1H), 5.11 (s, 2H), 3.69 (s, 2H); LCMS method (A), RT=4.2 min.

Example 10

Preparation of 2-(5-benzyloxy-4'-trifluoromethyl-biphenyl-3-yl)-pentanoic Acid (VIII)

(5-Benzyloxy-4'-trifluoromethyl-biphenyl-3-yl)-acetic acid (0.09 g, 0.23 mmol) in THF (1.2 ml) was added dropwise to a solution of LHMDS in hexanes (0.49 ml, 0.49 mmol, 1.0M) at −15° C. After 30 min iodopropane (0.08 ml, 0.82 mmol) in THF (0.3 ml) was added and the mixture was stirred for a further 30 min at −15° C. The mixture was then quenched by pouring onto a mixture of ice and HCl solution (2M aq). This was then extracted with EtOAc (×2), washed with NaHSO$_3$ solution (10% aq) and the organics were dried (MgSO$_4$) and then concentrated in vacuo to afford a yellow oil. The oil was purified by flash column chromatography (EtOAc:petroleum ether) to afford 2-(5-benzyloxy-4'-trifluoromethyl-biphenyl-3-yl)-pentanoic acid (0.016 g, 0.04 mmol) in 18% yield. $^1$H NMR (CDCl$_3$) δ 7.69-7-63 (m, 4H), 7.47-7.42 (m, 2H), 7.40 (t, 2H), 7.35-7.31 (m, 1H), 7.13-7.09 (m, 2H), 7.01-6.99 (m, 1H), 5.11 (s, 2H), 3.63-3.59 (m, 1H), 2.11-2.03 (m, 1H), 1.84-1.75 (m, 1H), 1.36-1.26 (m, 2H) 0.92 (t, 3H); LCMS method (A), (M-H$^-$) 385, RT=4.9 min.

Example 11

Preparation of (5-benzyloxy-3',5'-dichloro-biphenyl-3-yl)-acetic Acid (IX)

Procedure as for example 9 replacing benzene boronic acid with 3,5-dichlorobenzene boronic acid. $^1$H NMR (CDCl$_3$) δ 7.30-7.55 (m, 8H), 7.05 (s, 2H), 6.92 (s, 1H), 5.11 (s, 2H), 3.69 (s, 2H); LCMS method (A), RT=5.0 min.

Example 12

Preparation of 5-benzyloxy-4'-trifluoromethyl-biphenyl-3-yl)-acetic Acid (X)

Procedure as for example 9 replacing benzene boronic acid with 4-trifluoromethyl-benzene boronic acid. $^1$H NMR (CDCl$_3$) δ 7.66 (m, 4H), 7.30-7.48 (m, 5H), 7.11 (s, 2H), 6.97 (s, 1H), 5.11 (s, 2H), 3.71 (s, 2H); LCMS method (A), RT=4.3 min.

Example 13

Preparation of (5-benzyloxy-3',5'-bis-trifluoromethyl-biphenyl-3-yl)-acetic Acid (XI)

Procedure as for example 9 replacing benzene boronic acid with 3,5-bistrifluoromethylbenzene boronic acid. $^1$H NMR (CDCl$_3$) δ 7.96 (br s, 2H), 7.85 (br s, 1H), 7.48-7.32 (m, 5H), 7.13-7.09 (m, 2H), 7.02-7.00 (m, 1H), 5.13 (s, 2H), 3.72 (s, 2H); LCMS method (A), RT=4.6 min.

Example 14

Preparation of (5-benzyloxy-3',4'-dichloro-biphenyl-3-yl)-acetic Acid (XII)

Procedure as for example 9 replacing benzene boronic acid with 3,4-dichlorobenzene boronic acid. $^1$H NMR (CDCl$_3$) δ 7.63 (d, 1H), 7.50-7.30 (m, 7H), 7.08-7.03 (m, 2H), 6.96-6.93 (m, 1H), 5.10 (s, 2H), 3.68 (s, 2H); LCMS method (A), RT=4.6 min.

Example 15

Preparation of (5-benzyloxy-4'-trifluoromethoxy-biphenyl-3-yl)-acetic Acid (XIII)

Procedure as for example 9 replacing benzene boronic acid with 4-trifluoromethoxybenzene boronic acid. $^1$H NMR (CDCl$_3$) δ 7.58-7.53 (m, 2H), 7.47-7.31 (m, 5H), 7.29-7.23 (m, 2H), 7.09-7.05 (m, 2H), 6.95-6.92 (m, 1H), 5.11 (s, 2H), 3.67 (s, 2H); LCMS method (A), RT=4.4 min.

Example 16

Preparation of (5-benzyloxy-3'-methoxy-biphenyl-3-yl)-acetic Acid (XIV)

Procedure as for example 9 replacing benzene boronic acid with 3-methoxybenzene boronic acid. $^1$H NMR (CDCl$_3$) δ 7.47-7.32 (m, 6H), 7.12-7.07 (m, 4H), 6.93-6.89 (m, 2H), 5.11 (s, 2H), 3.85 (s, 3H), 3.69 (s, 2H); LCMS method (A), RT=4.2 min.

Example 17

Preparation of (5-benzyloxy-3'-carbamoyl-biphenyl-3-yl)-acetic Acid (XV)

Procedure as for example 9 replacing benzene boronic acid with benzamide-3-boronic acid. $^1$H NMR (CDCl$_3$) δ 12.30-12.45 (br, 1H), 8.13 (s, 2H), 7.87-7.79 (m, 2H), 7.56-7.22 (m, 8H), 6.97 (s, 1H), 5.18 (s, 2H), 3.63 (s, 2H); LCMS method (A), RT=3.6 min.

Example 18

Preparation of (5-benzyloxy-3'-hydroxy-biphenyl-3-yl)-acetic Acid (XVI)

Procedure as for example 9 replacing benzene boronic acid with 3-hydroxybenzene boronic acid. $^1$H NMR (CDCl$_3$) δ 7.45-7.28 (m, 6H), 7.13-7.08 (m, 3H), 7.01 (s, 1H), 6.91 (s, 1H), 6.97 (s, 1H), 6.82-6.08 (m, 1H) 5.09 (s, 2H), 3.67 (s, 2H); LCMS method (A), RT=3.8 min.

Example 19

Preparation of (5-benzyloxy-4'-methanesulfonyl-biphenyl-3-yl)-acetic Acid (XVII)

Procedure as for example 9 replacing benzene boronic acid with 4 methanesulphonylbenzene boronic acid. $^1$H NMR (CDCl$_3$) δ 7.98 (d, 2H), 7.74-7.72 (d, 2H), 7.46-7.35 (m, 5H), 7.13-7.12 (m, 2H), 7.00 (s, 1H) 5.12 (s, 2H), 3.71 (s, 2H), 3.09 (s, 3H); LCMS method (A), RT=3.8 min.

Example 20

Preparation of (5-benzyloxy-4'-sulfamoyl-biphenyl-3-yl)-acetic Acid (XVIII)

Procedure as for example 9 replacing benzene boronic acid with benzenesulfonamide-4-boronic acid pinacol ester. $^1$H NMR (CDCl$_3$) δ 7.89-7.83 (m, 4H), 7.49-7.21 (m, 9H), 7.00 (s, 1H), 5.17 (s, 2H), 3.62 (s, 2H); LCMS method (A), RT=3.6 min.

Example 21

Preparation of 2-(5-benzyloxy-4'-trifluoromethyl-biphenyl-3-yl)-propionic Acid (XIX)

Procedure as for example 10 replacing propyl iodide with methyl iodide. $^1$H NMR (CDCl$_3$) δ 7.70-7.62 (m, 4H), 7.48-7.30 (m, 5H), 7.15-7.09 (m, 2H) 7.02-7.00 (m, 1H), 5.12 (s, 2H), 3.80 (q, 1H), 1.56 (d, 3H); LCMS method (B), RT=12.3 min.

Example 22

Preparation of 2-(5-benzyloxy-4'-trifluoromethyl-biphenyl-3-yl)-2-methyl-propionic Acid (XX)

Preparation of methyl-2-(5-benzyloxy-4'-trifluoromethyl-biphenyl-3-yl)-2-methyl-propionate (5-Benzyloxy-4'-trifluoromethyl-biphenyl-3-yl)-acetic acid methyl ester (0.15 g, 0.37 mmol) in DMF (1.5 ml) was added dropwise to a suspension of NaH (0.072 g of a 60% suspension in mineral oil, 1.79 mmol) in DMF (1 ml) at −4° C. and the mixture was stirred for 1 h before methyl iodide (0.12 ml, 1.86 mmol) was added. The reaction was stirred between 4° C. and 0° C. for 2.5 h, diluted with DMF and warmed up to room temperature overnight. NH$_4$Cl solution (sat aq) was carefully added and the mixture was extracted with EtOAc. The combined organic extracts were washed with brine, dried (MgSO$_4$), filtered and concentrated under reduced pressure. The residue was purified by flash column chromatography (EtOAc:petroleum ether) to give 2-(5-benzyloxy-4'-trifluoromethyl-biphenyl-3-yl)-2-methyl-propionic acid methyl ester (0.12 g, 0.28) as colourless oil in 76% yield. $^1$H NMR (CDCl$_3$) δ 7.67 (m, 4H), 7.47 (m, 2H), 7.41 (m, 2H), 7.36 (m, 1H), 1.13 (m, 1H), 7.07 (m, 1H), 7.00 (m, 1H), 5.12 (s, 2H), 3.66 (s, 3H), 1.61 (s, 6H); LCMS method (3), RT=5.6 min.

Preparation of 2-(5-benzyloxy-4'-trifluoromethyl-biphenyl-3-yl)-2-methyl-propionic Acid A solution of 2-(5-benzyloxy-4'-trifluoromethyl-biphenyl-3-yl)-2-methyl-propionic acid methyl ester (0.12 g, 0.28 mmol) in THF (4 ml) was treated at room temperature with a solution of KOH (0.17 g, 3.00 mmol) in methanol and water (3 ml, 6:1). After two days the mixture was acidified with citric acid and extracted with EtOAc. The combined organic extracts were washed with NaHCO$_3$ solution (sat aq), brine, dried (MgSO$_4$), filtered and concentrated under reduced pressure. The residue was purified by flash column chromatography (EtOAc:petroleum ether) to give 2-(5-benzyloxy-4'-trifluoromethyl-biphenyl-3-yl)-2-methyl-propionic acid (0.045 g, 0.11 mmol) as a white solid in 39% yield. $^1$H NMR (d$_4$-MeOD) 7.79-7.71 (m, 4H), 7.50-7.46 (m, 2H), 7.42-7.36 (m, 2H), 7.35-7.29 (m, 1H), 7.25-7.23 (m, 1H), 7.17-7.14 (m, 1H), 7.08-7.05 (m, 1H), 5.17 (s, 2H), 1.59 (s, 6H); LCMS method (A), RT=4.5 min.

Example 23

Preparation of 1-(5-benzyloxy-4'-trifluoromethyl-biphenyl-3-yl)-cyclopropanecarboxylic Acid (XXI)

Procedure as for example 22 replacing methyl iodide with 1,2-dibromoethane. 1-(5-benzyloxy-4'-trifluoromethyl-biphenyl-3-yl)-cyclopropanecarboxylic acid was obtained as a white solid. $^1$H NMR (d6-DMSO) 7.90 (d, 2H), 7.80 (d, 2H), 7.49 (d, 2H), 7.41 (t, 2H), 7.37-7.31 (m, 1H), 7.27-7.23 (m, 2H), 7.07-7.02 (m, 1H), 5.19 (s, 2H), 1.49-1.43 (m, 2H), 1.25-1.20 (m, 2H); LCMS method (A), RT=4.7 min.

In an analogous fashion to example 9, replacing benzene boronic acid with the appropriate boronic acid, the following were synthesised:

| Example No | Name | LC Method | Retention Time (min) |
|---|---|---|---|
| 24 | (5-Benzyloxy-4'-fluoro-biphenyl-3-yl)-acetic acid (XXII) | A | 4.2 |
| 25 | (5-Benzyloxy-4'-chloro-biphenyl-3-yl)-acetic acid (XXIII) | A | 4.4 |
| 26 | (4'-Acetylamino-5-benzyloxy-biphenyl-3-yl)-acetic acid (XXIV) | B | 9.1 |
| 27 | (5-Benzyloxy-4'-hydroxy-biphenyl-3-yl)-acetic acid (XXV) | B | 9.4 |
| 28 | (5-Benzyloxy-4'-isopropoxy-biphenyl-3-yl)-acetic acid (XXVI) | B | 11.9 |
| 29 | (5-Benzyloxy-3',5'-difluoro-biphenyl-3-yl)-acetic acid (XXVII) | C | 3.2 |
| 30 | (5-Benzyloxy-3'-isopropoxy-biphenyl-3-yl)-acetic acid (XXVIII) | A | 4.4 |
| 31 | (5-Benzyloxy-4'-methoxy-biphenyl-3-yl)-acetic acid (XXIX) | B | 10.9 |
| 32 | (5-Benzyloxy-2'-methoxy-biphenyl-3-yl)-acetic acid (XXX) | B | 11.0 |
| 33 | (5-Benzyloxy-2'-methyl-biphenyl-3-yl)-acetic acid (XXXI) | B | 11.5 |
| 34 | (5-Benzyloxy-3'-methyl-biphenyl-3-yl)-acetic acid (XXXII) | B | 11.6 |
| 35 | (5-Benzyloxy-3'-trifluoromethyl-biphenyl-3-yl)-acetic acid (XXXIII) | B | 11.8 |
| 36 | (5-Benzyloxy-2'-fluoro-biphenyl-3-yl)-acetic acid (XXXIV) | A | 4.2 |
| 37 | (5-Benzyloxy-4'-methyl-biphenyl-3-yl)-acetic acid (XXXV) | C | 3.2 |
| 38 | (5-Benzyloxy-3'-fluoro-biphenyl-3-yl)-acetic acid (XXXVI) | C | 3.1 |
| 39 | (5-Benzyloxy-3'-chloro-biphenyl-3-yl)-acetic acid (XXXVII) | C | 3.3 |
| 40 | (5-Benzyloxy-3'-trifluoromethoxy-biphenyl-3-yl)-acetic acid (XXXVIII) | C | 3.3 |

Example 41

Preparation of 2-{5-[4-(pyrrolidine-1-sulfonyl)-benzyloxy]-4'-trifluoromethyl-biphenyl-3-yl}-pentanoic Acid (XXXIX)

Procedure as for example 110 replacing (5-benzyloxy-4'-trifluoromethyl-biphenyl-3-yl)-acetic acid with 5-[4-(pyrrolidine-1-sulfonyl)-benzyloxy]-4'-trifluoromethyl-biphenyl-3-yl-acetic acid, itself made according to the procedure of example 9 replacing benzyl alcohol with 4-(pyrrolidine-1-sulfonyl)-benzyl alcohol, afforded 2-{5-[4-(pyrrolidine-1-sulfonyl)-benzyloxy]-4'-trifluoromethyl-biphenyl-3-yl}-pentanoic acid, LC method B, retention time 12.6 min.

Example 42

Preparation of 2-(5-cyclopropylmethoxy-4'-trifluoromethyl-biphenyl-3-yl)-pentanoic Acid (XL)

Procedure as for example 10 replacing (5-benzyloxy-4'-trifluoromethyl-biphenyl-3-yl)-acetic acid with 5-cyclopropylmethoxy-4'-trifluoromethyl-biphenyl-3-yl-acetic acid, itself made according to the procedure of example 9 replacing benzyl alcohol with cyclopropylmethyl alcohol afforded 2-(5-cyclopropylmethoxy-4'-trifluoromethyl-biphenyl-3-yl)-pentanoic acid, LC method B, retention time 12.8 min.

Example 43

Preparation of [5-(4-chloro-benzyloxy)-4'-trifluoromethyl-biphenyl-3-yl]-acetic Acid (XLI)

To a solution of (5-benzyloxy-4'-trifluoromethyl-biphenyl-3-yl)-acetic acid (2.5 g, 5.5 mmol) in EtOH (50 mL) was added 10% Pd/C (5% wt) and the resultant black suspension stirred under an atmosphere of H$_2$ for 5 hours. The resultant mixture was filtered through celite and evaporated to dryness. The residue was purified by flash column chromatography (EtOAc:petroleum ether) to give 2.3 g (93%) (5-hydroxy-4'-trifluoromethyl-biphenyl-3-yl)-acetic acid ethyl ester as a white solid.

A suspension of (5-hydroxy-4'-trifluoromethyl-biphenyl-3-yl)-acetic acid ethyl ester (70 mg, 0.22 mmol), K$_2$CO$_3$ (60 mg, 2.0 equivalents), 4-chlorobenzyl bromide (50 mg, 1.1 equivalents) in MeCN (2 mL) was heated at 80° C. for 2 hours. The resultant suspension was filtered and evaporated to dryness. The residue was purified by flash column chromatography (EtOAc:petroleum ether) to give 85 mg (83%) [5-(4-chloro-benzoxy)-4'-trifluoromethyl-biphenyl-3-yl]-acetic acid ethyl ester as a clear oil.

[5-(4-Chloro-benzoxy)-4'-trifluromethyl-biphenyl-3-yl]-acetic acid ethyl ester (3) (85 mg, 0.19 mmol) was hydrolysed as described in example 9 to give 71 mg (90%) [5-(4-Chloro-benzyloxy)-4'-trifluoromethyl-biphenyl-3-yl]-acetic acid as a white solid. LC method C, retention time 3.4 min.

In an analogous fashion, using the appropriate halide as alkylating agent, the following were prepared:

| Example No | Name | LC method | retention time (min) |
|---|---|---|---|
| 44 | (5-Cyclopropylmethoxy-4'-trifluoromethyl-biphenyl-3-yl)-acetic acid (XLII) | A | 4.3 |
| 45 | [5-(5-Methyl-isoxazol-3-ylmethoxy)-4'-trifluoromethyl-biphenyl-3-yl]-acetic acid (XLIII) | A | 4.0 |
| 46 | [5-(3,5-Dichloro-benzyloxy)-4'-trifluoromethyl-biphenyl-3-yl]-acetic acid (XLIV) | A | 5.0 |
| 47 | [5-(Tetrahydro-pyran-4-ylmethoxy)-4'-trifluoromethyl-biphenyl-3-yl]-acetic acid (XLV) | A | 4.2 |
| 48 | [5-(4-Dimethylsulfamoyl-benzyloxy)-4'-trifluoromethyl-biphenyl-3-yl]-acetic acid (XLVI) | A | 4.1 |
| 49 | [5-(1-Phenyl-ethoxy)-4'-trifluoromethyl-biphenyl-3-yl]-acetic acid (XLVII) | A | 4.5 |
| 50 | {5-[4-(Morpholine-4-carbonyl)-benzyloxy]-4'-trifluoromethyl-biphenyl-3-yl}-acetic acid (XLVIII) | C | 2.9 |
| 51 | [4'-Trifluoromethyl-5-(3-trifluoromethyl-benzyloxy)-biphenyl-3-yl]-acetic acid (XLIX) | C | 3.4 |
| 52 | [4'-Trifluoromethyl-5-(2-trifluoromethyl-benzyloxy)-biphenyl-3-yl]-acetic acid (L) | C | 3.4 |
| 53 | (5-Phenethyloxy-4'-trifluoromethyl-biphenyl-3-yl)-acetic acid (LI) | C | 3.3 |
| 54 | [5-(Tetrahydro-pyran-2-ylmethoxy)-4'-trifluoromethyl-biphenyl-3-yl]-acetic acid (LII) | C | 3.1 |
| 55 | [5-(4-Dimethylcarbamoyl-benzyloxy)-4'-trifluoromethyl-biphenyl-3-yl]-acetic acid (LIII) | C | 2.9 |
| 56 | [5-(4-Methylcarbamoyl-benzyloxy)-4'-trifluoromethyl-biphenyl-3-yl]-acetic acid (LIV) | C | 2.8 |
| 57 | {5-[4-(Pyrrolidine-1-carbonyl)-benzyloxy]-4'-trifluoromethyl-biphenyl-3-yl}-acetic acid (LV) | C | 3.0 |
| 58 | {5-[4-(Morpholine-4-sulfonyl)-benzyloxy]-4'-trifluoromethyl-biphenyl-3-yl}-acetic acid (LVI) | C | 3.1 |
| 59 | [5-(4-Trifluoromethoxy-benzyloxy)-4'-trifluoromethyl-biphenyl-3-yl]-acetic acid (LVII) | C | 3.2 |
| 60 | [5-(2-Chloro-benzyloxy)-4'-trifluoromethyl-biphenyl-3-yl]-acetic acid (LVIII) | C | 3.4 |
| 61 | [5-(3-Chloro-benzyloxy)-4'-trifluoromethyl-biphenyl-3-yl]-acetic acid (LIX) | C | 3.4 |
| 62 | [5-(4-Methyl-benzyloxy)-4'-trifluoromethyl-biphenyl-3-yl]-acetic acid (LX) | C | 3.4 |

Example 63

Preparation of 2-(5-benzyloxy-4'-trifluoromethyl-biphenyl-3-yl)-pent-4-enoic Acid (LXI)

Preparation according to example 10 replacing iodopropane with allyl iodide afforded 2-(5-benzyloxy-4'-trifluoromethyl-biphenyl-3-yl)-pent-4-enoic acid, LC method C, retention time 3.5 min.

Example 64

Preparation of (R)-2-(5-Cyclopropylmethoxy-4'-trifluoromethyl-biphenyl-3-yl)-pentanoic Acid (LXII) and (S)-2-(5-Cyclopropylmethoxy-4'-trifluoromethyl-biphenyl-3-yl)-pentanoic Acid (LXIII)

The enantiomers of 2-(5-cyclopropylmethoxy-4'-trifluoromethyl-biphenyl-3-yl)-pentanoic acid were separated on a 5 cm Chiralpak AD column with 70/30 heptane/isopropanol with 0.1% acetic acid as the eluent at a flow rate of 80 ml/min. The first peak off the column was designated R* and the second peak S*.

Example 65

Preparation of (R)-2-(5-Benzyloxy-4'-trifluoromethyl-biphenyl-3-yl)-pentanoic Acid (LXIV) and (S)-2-(5-Benzyloxy-4'-trifluoromethyl-biphenyl-3-yl)-pentanoic Acid (LXV)

The enantiomers of 2-(5-Benzyloxy-4'-trifluoromethyl-biphenyl-3-yl)-pentanoic acid were separated on a 3 cm Chiralpak AD with methanol and 0.1% TFA as the eluent at a flow rate of 30 ml/min. The first peak off the column at 16 min was designated R* and the 2nd peak at 26 min was designated S*.

Example 66

Screening of the Compounds of the Invention for γ-Secretase-Modulating Activity

Screening was carried out using SKN neuroblastoma cells carrying the APP 695—wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

IC50-Values of Selected Compounds of the Invention on the γ-Secretase Activity.

The following compounds show an IC50 of <10 uM:
(R)-2-(5-Cyclopropylmethoxy-4'-trifluoromethyl-biphenyl-3-yl)-pentanoic acid;
(S)-2-(5-Cyclopropylmethoxy-4'-trifluoromethyl-biphenyl-3-yl)pentanoic acid;
(R)-2-(5-Benzyloxy-4'-trifluoromethyl-biphenyl-3-yl)-pentanoic acid;
(S)-2-(5-Benzyloxy-4'-trifluoromethyl-biphenyl-3-yl)-pentanoic acid.

Example 67

Demonstration of CNS Penetration

In-vivo Study: A total number of 24 mice (C57) were dosed orally at 100 mg/kg of drug compound in 10% propylene glycol, 7.5% ethanol and 82.5% solutol. At designated times (2, 4 and 8 his), a group of eight mice were sacrificed, and plasma and brain tissue samples were collected by following the NIH guideline.

Bioanalytical: Plasma samples were prepared as follows. Two hundred microliters of acetonitrile containing internal standard was added to 100 μL of plasma to precipitate proteins. After vortexing, samples were centrifuged at 10000 g for 10 min and supernatants were transferred to HPLC sample vials for analysis by LC-MS-MS. Calibration standards were prepared by adding appropriate volumes of drug stock solution directly into blank plasma (from untreated animals) and processed identically to collected plasma samples.

Brain tissues were first homogenized in two-volume of PBS buffer (e.g. 100 mg tissue in 200 μL PBS). Two hundred microliters of acetonitrile containing internal standard was added to 100 μL of tissue homogenants to precipitate proteins. Three replicates were processed for each tissue homogenant. After vortexing, samples were centrifuged at 10000 g for 10 min and supernatants were transferred to HPLC sample vials for analysis by LC-MS-MS. Calibration standards were prepared by adding appropriate volumes of stock solution directly into blank brain tissue homogenant (from untreated animals) and processed identically to collected plasma samples LC-MS-MS analysis was performed on operated in ESI positive ion mode. A generic LC gradient was utilized as 95% aqueous to 95% acetonitrile on a Sciex 4000 triple-quadrupole mass spectrometer interfaced to an Agilent. 1100 HPLC system. The mass spectrometer was over 11 minutes.

Under the above conditions the % ratio of brain to plasma concentration was 28.6 for (R*)-2-(5-benzyloxy-4'-trifluoromethyl-biphenyl-3-yl)-pentanoic acid and 32.0 for (S*)-2-(5-benzyloxy-4'-trifluoromethyl-biphenyl-3-yl)-pentanoic acid.

Example 68

Demonstration of In Vivo Efficacy

Aβ42 lowering agents of the invention can be used to treat AD in mammal such as a human or alternatively in a validated animal model such as the mouse, rat, or guinea pig. The mammal may not be diagnosed with AD, or may not have a genetic predisposition for AD, but may be transgenic such that it overproduces and eventually deposits Aβ in a manner similar to that seen in the human.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood plasma, CSF, or brain.

To determine whether acute administration of an Aβ42 lowering agent would reduce Aβ42 levels in-vivo, two-three month old Tg2576 mice expressing APP695 containing the "Swedish" variant can be used or alternatively a transgenic mouse model developed by Dr. Fred Van Leuven (K.U.Leuven, Belgium) and co-workers, with neuron-specific expression of a clinical mutant of the human amyloid precursor protein [V717I] (Moechars et al., 1999 J. Biol. Chem. 274, 6483). The commercial rights on this model have been transferred to reMYND NV. The single transgenic mouse displays spontaneous, progressive accumulation of β-amyloid (Aβ) in brain, eventually resulting in amyloid plaques within subiculum, hippocampus and cortex. Animals of this age have high levels of Aβ in the brain but no detectable Aβ deposition.

Mice treated with the Aβ42 lowering agent will be examined and compared to those untreated or treated with vehicle and brain levels of soluble Aβ42 and total Aβ would be quantitated by standard techniques, for example, using ELISA. Treatment periods may vary from hours to days and will be adjusted based on the results of the Aβ42 lowering once a time course of onset of effect can be established.

A typical protocol for measuring Aβ42 lowering in vivo is shown but it is only one of many variations that could be used to optimize the levels of detectable Aβ. For example, Aliquots of compounds can be dissolved in DMSO (volume equal to 1/10th of the final formulation volume), vortexed and further diluted (1:10) with a 10% (w/v) hydroxypropyl β cyclodextrin (HBC, Aldrich, Ref No 33,160-7) solution in PBS, where after they are sonicated for 20 seconds.

Aβ42 lowering agents may be administered as a single oral given three-four hours before sacrifice and analysis or alternatively could be given over a course of days and the animals sacrificed three to four hours after the final dose is given.

Blood is collected at sacrifice. The blood collection is performed via a heart puncture during anesthesia with a mixture of Ketalar (Ketamin), Rompun (Xylazin 2%) and Atropin (2:1:1) and collected in EDTA treated collection tubes. Blood is centrifuged at 4000 g for 5 minutes at 4° C. aid die plasma recovered for analysis.

The mice are anaesthetized with a mixture of Ketalar (Ketamin), Rompun (Xylazin 2%) and Atropin (2:1:1) and flushed trans-cardially with physiological serum at 4° C.

The brain is removed from the cranium and hindbrain and forebrain are separated with a cut in the coronal/frontal plane. The cerebellum is removed. The forebrain is divided evenly into left and right hemisphere by using a midline sagital cut.

One hemisphere is immediately immersed in liquid nitrogen and stored at −70° C. until homogenization for biochemical assays.

Brains are homogenized using a Potter, a glass tube (detergent free, 2 cm3) and a mechanical homogenizer (650 rpm). A volume of 6.5×½ brain weight of fleshly prepared 20 mM Tris/HCl buffer (pH 8.5) with Proteinase Inhibitors (1 tablet per 50 ml Tris/HCl buffer, Complete™, Roche, Mannheim, Germany) is used as homogenization buffer.

Samples are transferred from −70° C. into a sample holder with liquid nitrogen and each individual sample is pre-warmed by incubation on the bench for a few seconds prior to homogenization. The homogenates are collected in Beckman centrifuge tubes TLX and collected on ice prior to centrifugation. Between two samples, the Potter and the glass tube are rinsed carefully with distilled water (AD) without detergents and dried with absorption paper.

Samples are centrifuged in a pre-cooled ultracentrifuge (Beckman, Mannheim, Germany) for 1 hour and 20 minutes at 48000 rpm (135.000×g) at 4° C. The supernatant (soluble fraction containing secreted APP and amyloid peptides) is separated from the pellet (membrane fraction containing membrane-bound APP-fragments and plaque-associated amyloid peptides in case of aged mice).

Small reversed phase columns (C18-Sep-Pack Vac 3 cc cartridges, Waters, Mass., MA) are mounted on a vacuum system and washed with 80% acetonitrile in 0.1% Trifluoroacetic acid (A-TFA) followed with 0.1% TFA twice. Then the samples are applied and the columns are washed successively with 5% and 25% A-TFA. Amyloid peptides are eluted with 75% A-TFA and the eluates are collected in. 2 ml tubes on ice. Eluates are freeze-dried in a speedvac concentrator (Savant, Farmingdale, N.Y.) overnight and resolved in 240 μl of the sample diluent furnished with the ELISA kits.

To quantify the amount of human Aβ-42 in the soluble fraction of the brain homogenates, commercially available Enzyme-Linked-Immunosorbent-Assay (LISA) kits are used (h Amyloid β42 ELISA high sensitive, The Genetics Company, Zurich, Switzerland). The ELISA is performed according to the manufacturer's protocol. Briefly, the standard (a dilution of synthetic Aβ1-42) and samples are prepared in a 96-well polypropylene plate without protein binding capacity (Greiner bio-one, Frickenhausen, Germany). The standard dilutions with final concentrations of 1000, 500, 250, 125, 62.5, 31.3 and 15.6 pg/ml and the samples are prepared in the sample diluent, furnished with the ELISA kit, to a final volume of 60 µl. Samples, standards and blancs (50 µl) are added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate is added, followed 30 minutes later by an addition of TMB/peroxide mixture, resulting in the conversion of the substrate into a colored product. This reaction is stopped by the addition of sulfuric acid (1M) and the color intensity is measured by means of photometry with an ELISA-reader with a 450 nm filter. Quantification of the Abeta content of the samples is obtained by comparing absorbance to a standard curve made with synthetic Aβ1-42.

In such a model at least 20% Aβ42 lowering compared to untreated animals would be advantageous.

The invention claimed is:

1. A compound having the general formula (I)

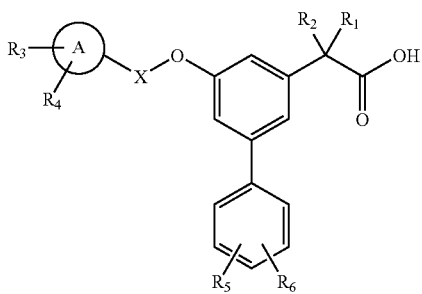

wherein

A is a ring selected from the group consisting of phenyl; $C_{3-7}$ cycloalkyl; and heterocyclyl;

X is a linear $C_1$-$C_4$ alkylene group which is optionally substituted with one or more substituents selected from the group consisting of F, Cl, Br, I and $C_1$-$C_4$ alkyl, wherein the $C_1$-$C_4$ alkyl group is optionally be substituted with one or more substituents selected from the group consisting of F, Cl, Br, and I;

$R_1$ and $R_2$ are each independently selected from the group consisting of H; alkyl selected from the group consisting of $CH_3$, $C_2H_5$, i-$C_3H_7$, n-$C_3H_7$, i-$C_4H_9$, n-$C_4H_9$, sec-$C_4H_9$, and tert-$C_4H_9$; and alkenyl selected from the group consisting of $C_2H_3$, i-$C_3H_5$, n-$C_3H_5$, n-$C_4H_7$, i-$C_4H_7$, and sec-$C_4H_7$; or $R_1$ and $R_2$ together form a ring, either saturated or unsaturated, with the carbon atom to which they are attached having 3-6 carbon atoms, which may contain in the ring one or more heteroatoms from the group N, S or O, wherein the heteroatoms may be identical or different if more than one heteroatom is present;

$R_3$, $R_4$, $R_5$ and $R_6$ are each independently selected from the group consisting of H; F; Cl; Br; I; CN; OH; C(O)N($R_7R_8$); S(O)$_2R_7$; SO$_2$N($R_7R_8$); S(O)N($R_7R_8$); N($R_7$)S(O)$_2R_8$; N($R_8$)S(O)$R_8$; S(O)$_2R_7$; N($R_7$)S(O)$_2$N($R_8R_{8a}$); S$R_7$; N($R_7R_8$); N($R_7$)C(O)$R_8$; N($R_7$)C(O)N($R_8R_{8a}$); N($R_7$)C(O)O$R_8$; OC(O)N($R_7R_8$); C(O)$R_7$; substituted or unsubstituted $C_1$-$C_4$-alkyl; and substituted or unsubstituted $C_1$-$C_4$-alkoxy; wherein the substituents of the $C_1$-$C_4$-alkyl and $C_1$-$C_4$-alkoxy groups are selected from the group consisting of F, Cl, Br, I, and $CF_3$; and $R_7$, $R_8$, and $R_{8a}$ are independently selected from the group consisting of H; $C_1$-$C_4$-alkyl; heterocyclyl; and $C_{3-7}$ cycloalkyl, wherein the $C_1$-$C_4$-alkyl, heterocyclyl, and $C_{3-7}$ cycloalkyl groups are optionally substituted with one or more substituents selected from the group consisting of F, Cl, Br, I and $CF_3$;

and/or a pharmaceutically acceptable salt or ester thereof.

2. The compound according to claim 1, wherein

A is phenyl; cyclopropyl; cyclohexyl; or a 6-membered aromatic heterocycle;

X is a $CH_2$ group which is optionally substituted with one or more substituents selected from the group consisting of F, Cl, Br, I and $C_1$-$C_4$ alkyl, wherein the $C_1$-$C_4$ alkyl group is optionally substituted with one or more substituent selected from the group consisting of F, Cl, Br, and I;

$R_1$ and $R_2$ are both H; $R_1$ is H and $R_2$ is $CH_3$, $C_2H_5$, i-$C_3H_7$, n-$C_3H_7$, i-$C_4H_9$, n-$C_4H_9$, sec-$C_4H_9$, or tert-$C_4H_9$; $R_1$ and $R_2$ are both $CH_3$; or $R_1$ and $R_2$ together from a cyclopropyl ring with the carbon atom to which they are attached; and $R_3$, $R_4$, $R_5$ and $R_6$ are each independently selected from the group consisting of H; F; Cl; Br; I; OH; C(O)NH$_2$; S(O)$_2$—$C_1$-$C_4$-alkyl; S(O)$_2$-heterocyclyl; $C_1$-$C_4$-alkyl; and $C_1$-$C_4$-alkoxy, wherein the $C_1$-$C_4$-alkyl and $C_1$-$C_4$-alkoxy groups may be substituted with at least one substituent selected from the group consisting of F, Cl, Br, and I.

3. The compound according to claim 2, wherein

A is phenyl;

X is $CH_2$ or $CHCH_3$; and $R_3$, $R_4$, $R_5$ and $R_6$ are each independently selected from the group consisting of H, F, Cl, OH, $CH_3$, $OCH_3$, $CF_3$, $OCF_3$, C(O)NH$_2$, S(O)$_2$—$C_1$-$C_4$-alkyl, and S(O)$_2$-heterocyclyl.

4. The compound according to claim 1, selected from the group consisting of

1) [5-(4-Fluoro-benzyloxy)-4'-trifluoromethyl-biphenyl-3-yl]-acetic acid;
2) [5-(4-Isopropyl-benzyloxy)-4'-trifluoromethyl-biphenyl-3-yl]-acetic acid;
3) [4'-Trifluoromethyl-5-(4-trifluoromethyl-benzyloxy)-biphenyl-3-yl]-acetic acid;
4) [5-(4-Methanesulfonyl-benzyloxy)-4'-trifluoromethyl-biphenyl-3-yl]-acetic acid;
5) (5-Cyclohexylmethoxy-4'-trifluoromethyl-biphenyl-3-yl)-acetic acid;
6) {5-[4-(Pyrrolidine-1-sulfonyl)-benzyloxy]-4'-trifluoromethyl-biphenyl-3-yl}-acetic acid;
7) (5-Benzyloxy-biphenyl-3-yl)-acetic acid;
8) 2-(5-Benzyloxy-4'-trifluoromethyl-biphenyl-3-yl)-pentanoic acid;
9) (5-Benzyloxy-3',5'-dichloro-biphenyl-3-yl)-acetic acid;
10) 5-Benzyloxy-4'-trifluoromethyl-biphenyl-3-yl)-acetic acid;
11) (5-Benzyloxy-3',5'-bis-trifluoromethyl-biphenyl-3-yl)-acetic acid;

12) (5-Benzyloxy-3',4'-dichloro-biphenyl-3-yl)-acetic acid;
13) (5-Benzyloxy-4'-trifluoromethoxy-biphenyl-3-yl)-acetic acid;
14) (5-Benzyloxy-3'-methoxy-biphenyl-3-yl)-acetic acid;
15) (5-Benzyloxy-3'-carbamoyl-biphenyl-3-yl)-acetic acid;
16) (5-Benzyloxy-3'-hydroxy-biphenyl-3-yl)-acetic acid;
17) (5-Benzyloxy-4'-methanesulfonyl-biphenyl-3-yl)-acetic acid;
18) (5-Benzyloxy-4'-sulfamoyl-biphenyl-3-yl)-acetic acid;
19) 2-(5-Benzyloxy-4'-trifluoromethyl-biphenyl-3-yl)-propionic acid;
20) 2-(5-Benzyloxy-4'-trifluoromethyl-biphenyl-3-yl)-2-methyl-propionic acid;
21) 1-(5-Benzyloxy-4'-trifluoromethyl-biphenyl-3-yl)-cyclopropanecarboxylic acid;
22) (5-Benzyloxy-4'-fluoro-biphenyl-3-yl)-acetic acid;
23) (5-Benzyloxy-4'-chloro-biphenyl-3-yl)-acetic acid;
24) (4'-Acetylamino-5-benzyloxy-biphenyl-3-yl)-acetic acid;
25) (5-Benzyloxy-4'-hydroxy-biphenyl-3-yl)-acetic acid;
26) (5-Benzyloxy-4'-isopropoxy-biphenyl-3-yl)-acetic acid;
27) (5-Benzyloxy-3',5'-difluoro-biphenyl-3-yl)-acetic acid;
28) (5-Benzyloxy-3'-isopropoxy-biphenyl-3-yl)-acetic acid;
29) (5-Benzyloxy-4'-methoxy-biphenyl-3-yl)-acetic acid;
30) (5-Benzyloxy-2'-methoxy-biphenyl-3-yl)-acetic acid;
31) (5-Benzyloxy-2'-methyl-biphenyl-3-yl)-acetic acid;
32) (5-Benzyloxy-3'-methyl-biphenyl-3-yl)-acetic acid;
33) (5-Benzyloxy-3'-trifluoromethyl-biphenyl-3-yl)-acetic acid;
34) (5-Benzyloxy-2'-fluoro-biphenyl-3-yl)-acetic acid;
35) (5-Benzyloxy-4'-methyl-biphenyl-3-yl)-acetic acid;
36) (5-Benzyloxy-3'-fluoro-biphenyl-3-yl)-acetic acid;
37) (5-Benzyloxy-3'-chloro-biphenyl-3-yl)-acetic acid;
38) (5-Benzyloxy-3'-trifluoromethoxy-biphenyl-3-yl)-acetic acid;
39) 2-{5-[4-(Pyrrolidine-1-sulfonyl)-benzyloxy]-4'-trifluoromethyl-biphenyl-3-yl}-pentanoic acid;
40) 2-(5-Cyclopropylmethoxy-4'-trifluoromethyl-biphenyl-3-yl)-pentanoic acid;
41) [5-(4-Chloro-benzyloxy)-4'-trifluoromethyl-biphenyl-3-yl]-acetic acid;
42) (5-Cyclopropylmethoxy-4'-trifluoromethyl-biphenyl-3-yl)-acetic acid;
43) [5-(5-Methyl-isoxazol-3-ylmethoxy)-4'-trifluoromethyl-biphenyl-3-yl]-acetic acid;
44) [5-(3,5-Dichloro-benzyloxy)-4'-trifluoromethyl-biphenyl-3-yl]-acetic acid;
45) [5-(Tetrahydro-pyran-4-ylmethoxy)-4'-trifluoromethyl-biphenyl-3-yl]-acetic acid;
46) [5-(4-Dimethylsulfamoyl-benzyloxy)-4'-trifluoromethyl-biphenyl-3-yl]-acetic acid;
47) [5-(1-Phenyl-ethoxy)-4'-trifluoromethyl-biphenyl-3-yl]-acetic acid;
48) {5-[4-(Morpholine-4-carbonyl)-benzyloxy]-4'-trifluoromethyl-biphenyl-3-yl}-acetic acid;
49) [4'-Trifluoromethyl-5-(3-trifluoromethyl-benzyloxy)-biphenyl-3-yl]-acetic acid;
50) [4'-Trifluoromethyl-5-(2-trifluoromethyl-benzyloxy)-biphenyl-3-yl]-acetic acid;
51) (5-Phenethyloxy-4'-trifluoromethyl-biphenyl-3-yl)-acetic acid;
52) [5-(Tetrahydro-pyran-2-ylmethoxy)-4'-trifluoromethyl-biphenyl-3-yl]-acetic acid;
53) [5-(4-Dimethylcarbamoyl-benzyloxy)-4'-trifluoromethyl-biphenyl-3-yl]-acetic acid;
54) [5-(4-Methylcarbamoyl-benzyloxy)-4'-trifluoromethyl-biphenyl-3-yl]-acetic acid;
55) {5-[4-(Pyrrolidine-1-carbonyl)-benzyloxy]-4'-trifluoromethyl-biphenyl-3-yl}-acetic acid;
56) {5-[4-(Morpholine-4-sulfonyl)-benzyloxy]-4'-trifluoromethyl-biphenyl-3-yl}-acetic acid;
57) [5-(4-Trifluoromethoxy-benzyloxy)-4'-trifluoromethyl-biphenyl-3-yl]-acetic acid;
58) [5-(2-Chloro-benzyloxy)-4'-trifluoromethyl-biphenyl-3-yl]-acetic acid;
59) [5-(3-Chloro-benzyloxy)-4'-trifluoromethyl-biphenyl-3-yl]-acetic acid;
60) [5-(4-Methyl-benzyloxy)-4'-trifluoromethyl-biphenyl-3-yl]-acetic acid;
61) 2-(5-Benzyloxy-4'-trifluoromethyl-biphenyl-3-yl)-pent-4-enoic acid;
62) (R)-2-(5-Cyclopropylmethoxy-4'-trifluoromethyl-biphenyl-3-yl)-pentanoic acid;
63) (S)-2-(5-Cyclopropylmethoxy-4'-trifluoromethyl-biphenyl-3-yl)-pentanoic acid;
64) (R)-2-(5-Benzyloxy-4'-trifluoromethyl-biphenyl-3-yl)-pentanoic acid;
65) (S)-2-(5-Benzyloxy-4'-trifluoromethyl-biphenyl-3-yl)-pentanoic acid;

and/or pharmaceutically acceptable salts or esters thereof.

5. A pharmaceutical composition comprising a compound of claim 1, in admixture with an inert carrier.

6. A compound of claim 1, wherein the compound is in the form of a pharmaceutically acceptable ester.

7. The compound of claim 1, wherein $R_1$ and $R_2$ in the compound are not both H.

8. A pharmaceutical composition comprising the compound of claim 1.

9. A pharmaceutical composition comprising the compound of claim 4.

10. A pharmaceutical composition comprising the compound of claim 4, and an inert carrier.

* * * * *